United States Patent
Molander et al.

(10) Patent No.: US 9,050,216 B2
(45) Date of Patent: Jun. 9, 2015

(54) ARTICLES COMPRISING IMPREGNATED THERMOPLASTIC MEMBERS AND METHOD OF MANUFACTURING THE ARTICLES

(71) Applicant: The Procter & Gamble Company, Cincinnati, OH (US)

(72) Inventors: John Carroll Molander, Cincinnati, OH (US); David Allan Wallack, Hillsboro, OR (US); Joseph Hung Lam, Ho Chi Minh (VN); Fred Naval Desai, Fairfield, OH (US); Urmish Popatal Dalal, Milford, OH (US); Mark James Kline, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/650,158

(22) Filed: Oct. 12, 2012

(65) Prior Publication Data
US 2013/0079739 A1    Mar. 28, 2013

Related U.S. Application Data

(60) Continuation of application No. 12/171,528, filed on Jul. 11, 2008, which is a division of application No. 10/288,144, filed on Nov. 5, 2002, now abandoned.

(60) Provisional application No. 60/338,761, filed on Nov. 5, 2001.

(51) Int. Cl.
| A61F 13/15 | (2006.01) |
| A61F 13/49 | (2006.01) |
| A61F 13/56 | (2006.01) |
| A61F 13/62 | (2006.01) |

(52) U.S. Cl.
CPC .............. *A61F 13/49* (2013.01); *A61F 13/5622* (2013.01); *A61F 13/15804* (2013.01); *A61F 13/62* (2013.01)

(58) Field of Classification Search
USPC ......... 604/399, 396, 387, 389, 390, 391, 392, 604/394
See application file for complete search history.

(56) References Cited

U.S. PATENT DOCUMENTS

| 3,758,657 A * | 9/1973 | Menzin et al. ................. 264/166 |
| 3,814,052 A * | 6/1974 | Caratsch ........................ 118/60 |

(Continued)

FOREIGN PATENT DOCUMENTS

| CN | 1315247 | 10/2001 |
| EP | 0 745 433 A1 | 12/1996 |

(Continued)

*Primary Examiner* — Jacqueline Stephens
(74) *Attorney, Agent, or Firm* — Sarah M. DeCristofaro; Abbey A. Lopez (57) ABSTRACT

An article, including disposable articles and durable articles, includes one or more shaped thermoplastic members, which can be at least partially impregnated into one or more fibrous substrates forming a composite material of the article having regions of breathability, elasticity, and/or stiffening to provide desired functions of the article. The shaped thermoplastic members have a profiled thickness and/or basis weight providing variation in material properties. A percent variation of the profiled thickness of the thermoplastic member can vary from about 5% to about 95%. A process for manufacturing the composite material of the present invention is also disclosed.

11 Claims, 6 Drawing Sheets

(56) References Cited

U.S. PATENT DOCUMENTS

| | | | |
|---|---|---|---|
| 4,300,562 A * | 11/1981 | Pieniak | 604/385.26 |
| 4,846,815 A * | 7/1989 | Scripps | 604/391 |
| 5,064,492 A | 11/1991 | Friesch | |
| 5,077,870 A * | 1/1992 | Melbye et al. | 24/452 |
| 5,137,537 A | 8/1992 | Herron et al. | |
| 5,230,851 A * | 7/1993 | Thomas | 264/145 |
| 5,260,015 A * | 11/1993 | Kennedy et al. | 264/167 |
| 5,326,415 A * | 7/1994 | Thomas et al. | 156/244.11 |
| 5,417,789 A | 5/1995 | Lauritzen | |
| 5,512,234 A * | 4/1996 | Takizawa et al. | 264/511 |
| 5,620,742 A * | 4/1997 | Lauritzen | 427/209 |
| 5,669,120 A * | 9/1997 | Wessels et al. | 24/446 |
| 5,792,411 A * | 8/1998 | Morris et al. | 264/400 |
| 5,833,804 A | 11/1998 | Ruppel et al. | |
| 5,938,648 A * | 8/1999 | LaVon et al. | 604/358 |
| 5,948,337 A * | 9/1999 | Sakakibara et al. | 264/167 |
| 6,176,850 B1 | 1/2001 | Rosenfeld et al. | |
| 6,248,419 B1 * | 6/2001 | Kennedy et al. | 428/100 |
| 6,287,665 B1 * | 9/2001 | Hammer | 428/100 |
| 6,432,098 B1 * | 8/2002 | Kline et al. | 604/387 |
| 6,627,133 B1 * | 9/2003 | Tuma | 264/167 |
| 6,827,806 B2 | 12/2004 | Uitenbroek et al. | |
| 6,942,894 B2 * | 9/2005 | Alberg et al. | 427/256 |
| 7,037,457 B2 * | 5/2006 | Seidel et al. | 264/267 |
| 2001/0016245 A1 * | 8/2001 | Tuman et al. | 428/99 |
| 2001/0037100 A1 * | 11/2001 | Shanklin | 604/358 |

FOREIGN PATENT DOCUMENTS

| | | | |
|---|---|---|---|
| EP | 0 622 127 B1 | 11/1997 | |
| EP | 0 923 921 A1 | 6/1999 | |
| EP | 1 104 692 A2 | 6/2001 | |
| EP | 1104692 A2 * | 6/2001 | B32B 5/26 |
| GB | 2 187 659 | 9/1987 | |
| WO | WO 99/11211 * | 3/1999 | A61F 13/56 |

* cited by examiner

ARTICLES COMPRISING IMPREGNATED THERMOPLASTIC MEMBERS AND METHOD OF MANUFACTURING THE ARTICLES

FIELD OF THE INVENTION

The present invention relates to disposable and durable articles, such as disposable diapers, pull-on diapers, incontinence briefs, feminine hygiene articles, baby bibs, and the like, and durable articles including sportswear, outerwear and the like, which comprise one or more thermoplastic members of polymeric materials impregnated into a fibrous substrate to provide desired properties, and a method of manufacturing thereof.

BACKGROUND

Disposable and durable articles require many specific material properties needed to provide desired performance functions, which are often difficult to provide using conventional methods of manufacture. For example, disposable absorbent articles, such as baby diapers, have many designs providing desired product performance in collecting and retaining urine and bowel movement (BM) without leaking outside the diaper. These functions need to be performed together with other functions in providing certain comfort to a wearer or user of the diaper during application, wear and disposal of the diaper. Comfort can be affected by effective functions of collecting and separating the exudates from the skin of the wearer, by providing a good initial fit of the diaper around the wearer and maintaining the fit during the use so the diaper does not sag and leak when becomes loaded with exudates.

Good fit around the body of the wearer is generally provided by creating elasticized areas in certain locations of the diaper. Examples of such elasticized areas include elastic leg cuffs, elastic waistband, elastic side panels, and others. The desired elastic properties in such areas are normally provided by various techniques, which generally include creation of composite materials by laminating elastic materials with nonwoven substrates. The elastic materials typically include an elastic film, single or multiple elastic strands, an elastic scrim, and the like. The elastic materials are typically bonded to nonwoven substrates by adhesives, thermal bonding, ultrasonic bonding, pressure bonding, and the like. However, this practice is expensive because it generally needs substantial amounts of elastic materials, which generally are considerably more expensive than nonwoven materials. Because elastic materials are typically bonded with nonwoven materials, the cost includes both the cost of adhesives and the cost of adhesive operations. Further, prior to the bonding of the elastic materials to the non-woven substrates, the elastic materials typically require process operations to form the elastic materials into desired sizes and shapes. Such operations can be called secondary operations and often include un-winding, feeding, cutting, slitting, gluing, and the like. Due to the physical properties of elastic materials, they are often difficult to handle, often requiring special modifications to make a specific elastic material process-friendly, i.e., easier to handle. Furthermore, these secondary operations often result in waste of elastic materials in the form of trim and/or scrap.

Further, with respect to the elasticized areas of the diaper, these areas often require profiled elasticity (varying elasticity), which is often difficult to provide. Examples of profiled areas of elasticity can include side panels, elastic waists, and leg elastic cuffs, providing both comfort and sustained fit.

Therefore, it would be beneficial to provide elasticized materials, comprising reduced amounts of elastic materials. Further, it would be beneficial to provide elasticized materials, production of which does not require the use of secondary operations. Further, it would be beneficial to provide elasticized materials having varying degrees of elasticity in desired areas of the product.

Good comfort during the wear and use of the diaper can be generally provided by use of breathable materials comprising the diaper. For example the outer cover of the diaper can be vapor permeable. Further, the diaper can be designed to have breathable, but liquid impervious elasticized cuffs around the legs; breathable elasticized waist; breathable elasticized side panels; and breathable but liquid-impervious backing layer. This is generally accomplished by bonding thermoplastic materials, like porous or nonporous films, scrims, or strands to a nonwoven substrate. Again, this approach incurs more cost for thermoplastic materials and secondary operations. Further, one important attribute of breathability is providing a varying degree of breathability in desired areas of the article. This is difficult and expensive to accomplish in utilizing the lamination technology. Therefore, it would be beneficial to provide breathable materials having varying degrees of breathability and comprising reduced amount of thermoplastic materials and which do not require the use of secondary operations described above.

Further, a disposable diaper that provides functions of collecting and retaining urine and BM without leakage outside the diaper requires a fastening system to allow for desired closure of the article around torso of the wearer. Examples of fastening systems include hook-and-loop fastener systems and adhesive tape fastening systems, which require substantial mass of thermoplastic material to provide desired material physical properties such as strength and stiffness. Another example of a fastening system includes the slot and tab fastener requiring specific shape or configuration, which is difficult to provide utilizing the lamination technology. Therefore, it would be beneficial to provide a material of the desired shape comprising less mass of thermoplastic material and does not require the secondary operations, described above.

Further, the fastening systems require varying degrees of stiffness and strength for both functional and comfort purposes. This is difficult to accomplish using the lamination technology because, as above, it requires more thermoplastic material and secondary operations. Therefore, it would be beneficial to provide a material having variable degree of stiffness and strength in specific areas comprising less mass of thermoplastic material and which does not require the secondary operations, as described above.

Further, the comfort of the wearer is affected by the surface texture of the material contacting the skin of the wearer and/or caregiver, as well as aesthetic appearance of the material itself. This is difficult to accomplish using lamination technology. In addition, it requires additional thermoplastic materials and secondary operations to mask undesirable characteristics of material surfaces. For example, an outer cover, which comprises a nonwoven web laminated to the outer surface of a thermoplastic film, provides a cloth-like appearance of the outer cover. Another example includes tapes comprising a nonwoven web laminated to the outer surface of a thermoplastic film to provide a cloth-like appearance. Therefore, it would be beneficial to provide a material having a desired surface texture and aesthetic appearance comprising less mass of thermoplastic material and which does not require secondary operations, as described above.

With respect to durable articles, the desired material properties such as elasticity, breathability, stiffness, strength and the like are difficult to provide using conventional manufacturing techniques including sewing, ultrasonic welding, and the like, of expensive fabrics having the desired properties. As disclosed above, these techniques require more material (thermoplastics and others) and secondary operations associated with cutting, sewing, and assembling. Therefore, it would be beneficial to substitute the expensive materials with less expensive materials comprising impregnated thermoplastic members having the desired properties and to reduce the secondary operations associated with cutting, handling, sewing, and bonding of durable articles.

SUMMARY OF THE INVENTION

In response to the difficulties and problems discussed above, a new article and a process for producing thereof have been discovered.

In one aspect, the present invention concerns an article including one or more shaped thermoplastic members at least partially impregnated into one or more fibrous substrates forming a composite material, wherein the shaped thermoplastic members have a profiled thickness providing variation in material properties, and wherein a percent variation of the profiled thickness of the thermoplastic member can vary from about 5% to about 95%.

In another aspect, the present invention concerns a method of making a composite material including at least one shaped thermoplastic member impregnated into at least one fibrous substrate, the method including the steps of:
 a) providing a first fibrous substrate;
 b) depositing a first thermoplastic material on the first fibrous substrate to form at least one shaped thermoplastic member having a profiled thickness providing variation in material properties, wherein a percent variation of the profiled thickness of the thermoplastic member can vary from about 5% to about 95%, and wherein the step of depositing is selected from a group consisting of intaglio printing, gravure printing, screen printing, ink jet printing, and flexographic printing;
 c) providing a second substrate; and
 d) combining the first substrate and the second substrate to form the composite material, wherein the thermoplastic member is at least partially impregnated into the first substrate.

In still another aspect, the present invention concerns a composite material including one or more shaped thermoplastic members, at least partially impregnated into one or more fibrous substrates forming the composite material, wherein the shaped thermoplastic members have a profiled thickness providing variation in material properties, and wherein a percent variation of the profiled thickness of the thermoplastic member can vary from about 5% to about 95%.

BRIEF DESCRIPTION SHOWN IN THE DRAWINGS

While the specification concludes with claims particularly pointing out and distinctly claiming the subject matter which is regarded as the present invention, it is believed that the invention will be more fully understood from the following description taken in conjunction with the accompanying drawings, in which:

DETAILED DESCRIPTION OF THE INVENTION

The article and the method of manufacture of the present invention can provide a surprising improvement in cost by reducing the need for thermoplastic materials and secondary process operations associated with cutting, forming, and bonding these materials to form a desired product. The article includes new composite materials comprising at least one thermoplastic member at least partially impregnated in one or more fibrous substrates of the article.

The impregnated thermoplastic members can have various basis weights and three dimensional shapes and profiles, which can result in desired variations in physical properties of the composite material. The planer shape in the x-y direction of the impregnated thermoplastic members can be any suitable geometrical shape defining the planer dimensions of the composite material, including a rectilinear outline, a curvilinear outline, a triangle, a trapezoid, a square, a parallelogram, a polygon, an ellipse, a circle, and any combination thereof. In the cross section of the member, its shape in the z direction can be any suitable geometric shape including linear and nonlinear profiles. The variation of the impregnated thermoplastic member in the z direction can be from about 5% to about 95%, preferably from about 20% to about 80%. The variation can extend in any direction in the x-y plane and can be calculated by the following formula:

$$\text{Percent variation} = 100 \times (\text{maximum thickness} - \text{minimum thickness})/\text{maximum thickness}.$$

The new composite materials of the present invention can have various material properties within the planer dimensions of the composite material, which can vary generally as a function of the variation in thickness of the impregnated polymeric member. The new composite materials can include such unique materials properties including a relatively high ratio of modulus of elasticity to density, a relatively high ratio of tensile strength to density, and other ratios provided by a unique combination of a first material (a substrate, fibrous material) and a second material (a thermoplastic member) impregnated within the fibers of the first material. The unique material property ratios result in cost benefits of the new composite materials. The lightness, flexibility, the tensile strength, the elasticity, porosity, and many other properties contemplated by the inventors can be provided by the first material of the composite material. The second material can be impregnated within the fibers of the first material, forming the composite material. The second material can be provided with various material properties within the realm of polymers. For example, a desired tensile strength, a modulus of elasticity, elasticity, electrical and/or thermal conductivity, air breathability, liquid impermeability, magnetism, and many other properties have been contemplated by the inventors. It should be noted that the inventors have contemplated many other utilizations of thermoplastic members and resulting composite materials. For example, one of the specific contemplated utilizations of the above properties of the thermoplastic members can be in providing various envisioned, desired functions of detecting bodily functions of a wearer, including temperature, skin condition, relative humidity between the skin and the article, presence of body extrudates, and the state of the capacity of the absorbent article.

Further, unique interrelationships between physical properties of the new composite materials can be formed, for example, a relatively high ratio of modulus to density, a relatively high ratio of tensile strength to density, providing cost benefits for the new composite material.

Similarly to the thickness profile described above, the basis weight of the composite material can also have a desirable profile. Similarly, the basis weight profile can be any suitable geometric shape including linear and nonlinear profiles. The variation in basis weight of the composite material of the present invention across the x-y plane can be from about 5% to about 95%, preferably from about 20% to about 80%, wherein this variation can be calculated by the following formula:

Percent variation=100×(maximum basis weight−minimum basis weight)/maximum basis weight.

TERMINOLOGY

The term "article" herein includes both disposable and durable articles.

The term "disposable" is used herein to describe products which generally are not intended to be laundered or otherwise restored or extensively reused in their original function, i.e., preferably they are intended to be discarded after about 10 uses or after about 5 uses or after about a single use. It is preferred that such disposable articles be recycled, composted or otherwise disposed of in an environmentally compatible manner.

The term "durable" is used herein to describe products which generally are intended to be laundered or otherwise restored or extensively reused in their original function, i.e., preferably they are intended to be used more than about 10 times.

A "disposable absorbent article" refers herein to a device that normally absorbs and retains fluids. In certain instances, the phrase refers to devices that are placed against or in proximity to the body of the wearer to absorb and contain the excreta and/or exudates discharged from the body, and includes such personal care articles as baby diapers, baby training pants, adult incontinence articles, feminine hygiene articles, baby swim diapers, wound dressing, and the like. In other instances, the phrase refers to protective articles, such as, for example, dining bibs that have the ability to absorb food items to prevent staining of the wearer's clothing.

The term "diaper" includes baby diapers, baby training pants, baby pool diapers, or adult incontinence articles and refers to a disposable fluid-handling article generally worn by infants and other incontinent persons about the lower torso.

The term "feminine hygiene articles" refers herein to any absorbent article worn by women to absorb and contain menses and other vaginal exudates.

A "body wrap" refers herein to an article or a garment worn about the body, typically to provide some therapeutic benefit, such as, for example, pain relief, wound coverage or to hold another device or article near the body.

The term "breathable" is used herein to describe materials that are permeable and transmittable to vapor, wherein the vapor transmission rate is measured in grams per 24 hours.

The term "material" refers herein to any web, substrate, fibrous material, woven, nonwoven, knitted, film, a component of a garment or an absorbent article.

The term "web" is meant herein any continuous material, including a film, a non-woven fabric, a woven fabric, a foam or a combination thereof, or a dry lap material including wood pulp, and the like, having a single layer or multiple layers.

The term "substrate" is meant herein any material, including a film, a non-woven fabric, a woven fabric, a foam or a combination thereof, or a dry lap material including wood pulp, and the like, having a single layer or multiple layers, and suitable for printing a polymeric material on at least one surface of the "substrate."

A "fibrous substrate" means herein a material comprised of a multiplicity of fibers that could be either a natural or synthetic material or any combination thereof. For example, nonwoven materials, woven materials, knitted materials, celluloid materials, and any combinations thereof.

The term "nonwoven" refers herein to a fabric made from continuous filaments and/or discontinuous fibers, without weaving or knitting by processes such as spun-bonding and melt-blowing. The non-woven fabric can comprise one or more nonwoven layers, wherein each layer can include continuous filaments or discontinuous fibers.

An "elastomer" refers herein to a polymer exhibiting elastic properties.

The term "elastic", "elastic properties" or "elasticized" refers herein to any material that upon application of a force to its relaxed, initial length can stretch or elongate to its elongated length without rupture and breakage, and which can substantially recover its initial length upon release of the applied force.

A "natural material" means herein a material derived from plants, animals, insects or byproducts of plants, animals, and insects. Non-limiting examples of natural materials useful in the disposable articles include celluloid fibers, cotton fibers, keratin fibers, silk fibers and the like. Non-limiting examples of celluloid fibers include wood pulp fibers, hemp fibers, jute fibers, and the like. Non-limiting examples of keratin fibers include wool fibers, camel hair fibers, and the like.

The term "stiffening region" refers herein to an area of a material having a greater modulus of elasticity than that of the adjacent areas of the material.

The term "elastic region" refers herein to an area of a material having greater elastic properties than those of the adjacent areas of the material.

The term "breathable region" refers herein to an area of a material having a greater breathability (measured in grams per meter per 24 hours of moisture vapor transmission rate MVTR) than that of the adjacent areas of the material.

Figure 1:
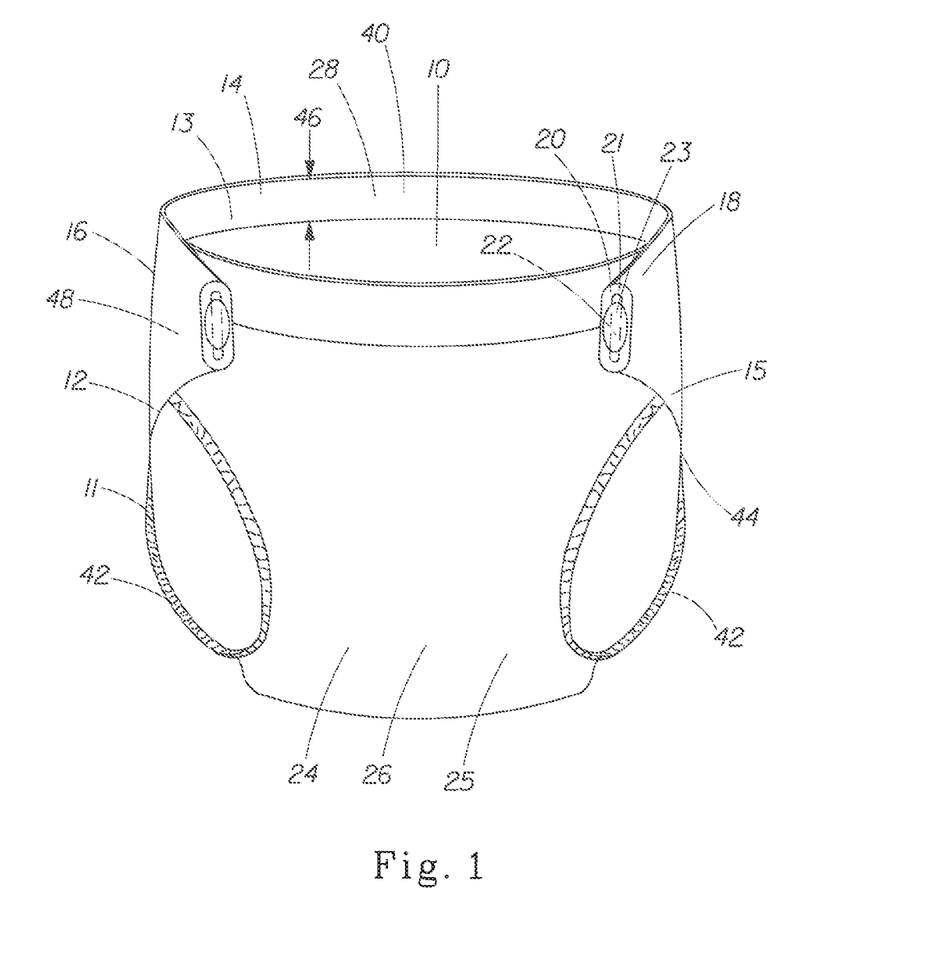
FIG. 1 is a perspective view of one embodiment of a disposable absorbent article of the present invention.

An article of the present invention can best be understood by reference to FIG. 1 illustrating one embodiment of an absorbent article of the present invention, specifically a disposable diaper 10. For ease of understanding, much of the following description will be made in terms of the disposable diaper 10. The diaper 10 can comprise a multiplicity of impregnated thermoplastic members into nonwoven substrates of the diaper 10, providing specific material properties and/or specific functions for the diaper 10, such as, for example, a gasketing function around the legs of the wearer provided by an elastic region 11 of the article expressed by a leg elastic 12; another gasketing function around the waist of the wearer provided another elastic region 13 of the article expressed by the waist elastic 14; a fit function around the torso provided another elastic region 15 expressed by an elasticized side panel 16; a fastening function that provides closure for the diaper 10 is provided by a stiffening region 21 and a stiffening region 23, expressed as a slot member 20 and tab member 22, respectively, capable of engaging to effect a desired closure; and a breathable function for the diaper 10, provided by a breathable region 25 expressed by the outer-cover 24 providing transmission of vapors through the outer-cover 24, as well as a barrier for liquids including waste exudates.

In order to provide the above functions for the product, the thermoplastic members impregnated into fibrous substrates result in new composite materials having a variety of unique properties contributed by the components of the new composite materials, which can provide desired physical properties at lower cost due to less polymeric materials than needed by conventional lamination technology. Because of the fibrous structure, the resulting composite materials have lighter weight and greater mechanical properties than the polymeric resin. The fibrous substrate provides desired structural fibrous network of generally interconnected fibers having desired tensile and stiffness properties. In addition, the percent fiber volume of the composite material can affect the mechanical properties in the composite material. The percent fiber volume is defined as the volume of fibers inside an impregnated member divided by the total volume of the impregnated member.

Figures 2, 3:
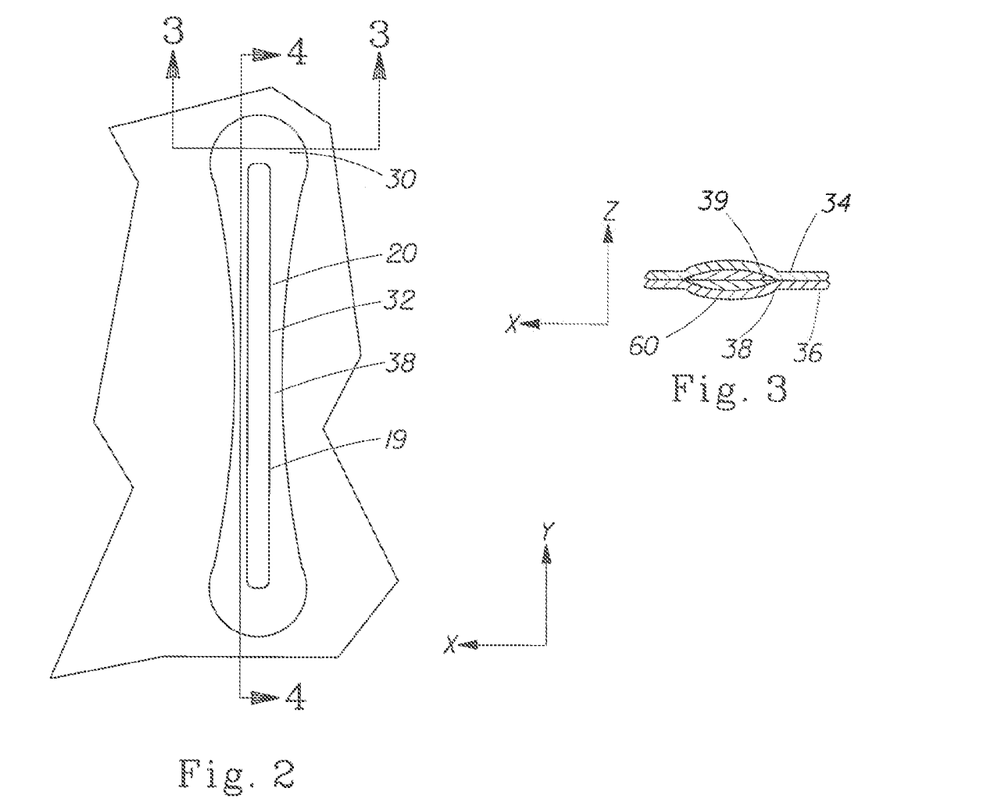
FIG. 2 is a magnified view of one embodiment of an impregnated thermoplastic member of the present invention.
FIG. 3 is a cross sectional view of the impregnated thermoplastic member shown in FIG. 2 taken along line 3-3.

FIG. 2 illustrates a magnified plan view of one embodiment of an impregnated thermoplastic member 30 of the present invention forming a void 19 defined by the slot member 20 of the fastening system 18 (FIG. 1). The void 19 is defined by a rectangular shape; however, the void 19 can be defined by any suitable geometrical shape including a rectilinear outline, a curvilinear outline, a triangle, a trapezoid, a square, a parallelogram, a polygon, an ellipse, a circle, and any combination thereof. The impregnated thermoplastic member 30 provides the desired rigidity and strength around a slot opening 32. The size of the impregnated thermoplastic member 30 can vary in x-y-z directions, preferably from millimeters to meters in x-y direction, and from microns to millimeters in the z direction. In one embodiment, the y dimension is 80 mm, the x dimension is 25 mm, and the z dimension can vary along the y-axis, from about 0.3 mm to about 1.0 mm in a desired profile that yields a 70% thickness variation in the z dimension. In another embodiment, the y dimension is 80 mm, the x dimension is 25 mm, and the z dimension along the y-axis can vary from 0.05 mm to about 1.0 mm in a desired profile that yields a 95% thickness variation in the z dimension. In yet another embodiment, the y dimension is 80 mm, the x dimension is 25 mm, and the z dimension along the y-axis can vary from 0.95 mm to about 1.0 mm in a desired profile that yields a 5% thickness variation in the z dimension. From the preceding embodiments one skilled in the art can see a wide range of thickness profile variation is possible with the present invention and all intermediate values within this range of about 5% to about 95% are also contemplated.

Properties of the composite material depend upon the individual properties of the polymeric member (resin), the individual properties of a fibrous substrate, and the volume of fiber impregnated into the polymeric member. In one embodiment of the present invention, the composite material of the slot and tab fastener system 18 (FIG. 1), including stiffening regions 21 and 23, comprises a polypropylene thermoplastic member 30 (FIG. 2) fabricated from a polypropylene resin such as BASELL 917 manufactured by Basell Polyolefins Company N.V. of the Netherlands and a polyester nonwoven substrate such as manufactured by DuPont of Delaware under brand name SONTARA. The BASELL 917 polypropylene resin has a modulus of elasticity of about 1200 MPa (Pascal×$10^6$), and SONTARA polyester nonwoven fibers have a modulus of elasticity of about 8900 MPa. The resulting composite material, comprising a fiber volume of SONTARA, ranging from about 10% to about 90%, can have a modulus of elasticity ranging from about 1700 MPa to about 8000 MPa, respectively, which is significantly greater than the modulus of elasticity of the thermoplastic polypropylene resin. In another embodiment of the present invention, the composite material of the slot and tab fastener system 18 comprises a polyethylene thermoplastic member fabricated from a polyethylene resin such as BASELL Lupolen 3020 manufactured by Basell Polyolefins Company N.V. of the Netherlands and a polyester nonwoven substrate such as manufactured by DuPont of Delaware under brand name SONTARA. The BASELL Lupolen 3020 polyethylene resin has a modulus of elasticity of about 300 MPa (Pascal×$10^6$), and SONTARA polyester nonwoven fiber have a modulus of elasticity of about 8900 MPa. The resulting composite material, comprising a fiber volume of SONTARA, ranging of about 10% to about 90%, can have a modulus of elasticity ranging from about 350 MPa to about 6000 MPa, which is significantly greater than the modulus of elasticity of the thermoplastic polyethylene resin.

From the preceding embodiments one skilled in the art can see a wide range of modulus of elasticity variation is possible with the present invention and all intermediate values within the full range of about 350 MPa to about 8000 MPa are also contemplated.

Further, in regards to the tensile strength of the fastener system 18, BASELL 917 polypropylene resin has a tensile strength of about 300 MPa, and SONTARA polyester nonwoven substrate fibers have tensile strength of about 1800 MPa. The resulting composite material comprising a fiber volume of about 10% to about 90% has a tensile strength range of about 400 MPa about 1600 MPa, which is significantly greater than the tensile strength of the thermoplastic polypropylene resin.

In another embodiment of the present invention, the composite material of the slot and tab fastener system 18 comprises a polyethylene thermoplastic member fabricated from a polyethylene resin such as BASELL Lupolen 3020 manufactured by Basell Polyolefins Company N.V. of the Netherlands and a polyester nonwoven substrate such as manufactured by DuPont of Delaware under brand name SONTARA. The BASELL Lupolen 3020 polyethylene resin has a tensile strength from about 15 MPa (Pascal×$10^6$), and SONTARA polyester nonwoven fibers have a tensile strength of about 1800 MPa. The resulting composite material, comprising a fiber volume of SONTARA ranging of about 10% to about 90%, can have a tensile strength of about 25 MPa to about 1600 MPa, which is significantly greater than the tensile strength of the thermoplastic polyethylene resin.

From the preceding embodiments one skilled in the art can see a wide range of tensile variation is possible with the present invention and all intermediate values within the full range of about 25 MPa to about 1600 MPa are also contemplated.

The profile of the impregnated thermoplastic member 30 (FIG. 1) can be any suitable geometric contour having a linear or nonlinear profile. FIG. 3 illustrates a cross sectional view of the impregnated thermoplastic member 30 shown in FIG. 2, taken along cross lines 3-3. The thermoplastic member 30 is preferably at least partially impregnated into both substrates 34 and 36, which are combined together to form a new composite material 38. In one embodiment, the cross section of the member 30 can have a generally uniform thickness in the z-direction with tapering 39 on the outer edges of the impregnated member 30. Tapering is desired to provide flexibility at the edges to prevent discomfort to the wearer from stiff edges.

Figure 4:
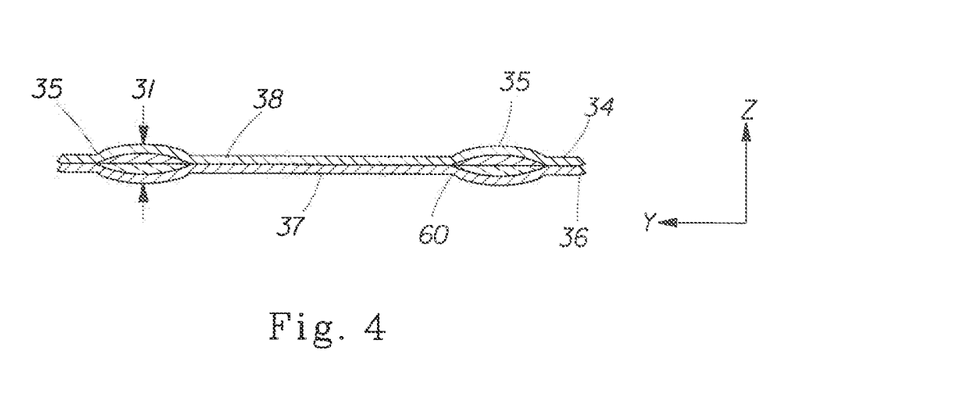
FIG. 4 is a cross sectional view of the impregnated thermoplastic member shown in FIG. 2 taken along line 4-4.

Similarly, FIG. 4 illustrates a cross sectional view of the impregnated thermoplastic member 30 taken along cross lines 4-4, having a profiled thickness 31. The shape of the profiled thickness 31 can be selected to provide a desired strength profile of the composite material 38, specifically, the shape of the profiled thickness varies to provide additional stiffness at the ends 35 of the impregnated thermoplastic member 30 and more flexibility in the middle 37 of the impregnated thermoplastic member 30.

The outer cover 24 of the diaper 10 shown in FIG. 1 includes a thermoplastic member 26 to provide desired breathability of the outer cover 24 while maintaining liquid impermeability of the outer cover 24. The thermoplastic member 26 can be made from a variety of polymeric resins providing vapor permeability and liquid impermeability across the z direction. Examples of such materials can include monolithic polyesters like HYTREL manufactured by DuPont of Delaware, polyolefin materials that can include particulates like calcium carbonate, and others. The level of breathability and liquid impermeability can vary across the outer cover 24 by varying the thickness of the impregnated thermoplastic member 26 in the z direction.

With respect to impermeability, in one embodiment of the present invention, the thermoplastic member 26 can be manufactured from HYTREL that is at least partially impregnated into a High Elongation Carded polypropylene nonwoven manufactured by BBA Nonwovens Inc. of South Carolina, having a basis weight of about 22 grams/meter$^2$. The resulting composite material can provide liquid impermeability from about 50 mm to about 700 mm of Hydrostatic Head. The thickness of the thermoplastic member 26 can vary from about 10 microns to about 35 microns for a 71% thickness variation, wherein a higher degree of impermeability can be provided in areas of greater thickness. For example, in the crotch area of diaper 10 where greater liquid impermeability is desired, the thickness of the thermoplastic member 26 can be greater than in other areas of the outer cover 24. From the preceding embodiment one skilled in the art can see a wide range of liquid impermeability variation is possible with this invention and all intermediate values within this range of about 50 mm to about 700 mm of Hydrostatic Head are also contemplated.

With respect to impermeability, in another embodiment of the present invention, the thermoplastic member 26 can be manufactured from HYTREL that is at least partially impregnated into a High Elongation Carded polypropylene nonwoven manufactured by BBA Nonwovens Inc. of South Carolina, having a basis weight of about 22 grams/meter$^2$. The resulting composite material can provide liquid impermeability from about zero grams/meter$^2$ to about 5 grams/meter$^2$ Dynamic Fluid Transmission at an impact energy of about 1000 Joules/meter$^2$. The thickness of the thermoplastic member 26 can vary from about 10 microns to about 35 microns for a 71% thickness variation, wherein a higher degree of impermeability can be provided in areas of greater thickness. For example, in the crotch area of diaper 10 where greater liquid impermeability is desired, the thickness of the thermoplastic member 26 can be greater than in other areas of the outer cover 24. From the preceding embodiment one skilled in the art can see a wide range of liquid impermeability variation is possible with this invention and all intermediate values within this range of about zero grams/meter$^2$ to about 5 grams/meter$^2$ Dynamic Fluid Transmission at an impact energy of about 1000 Joules/meter$^2$ are also contemplated.

With respect to breathability, in one embodiment of the present invention, the thermoplastic member 26 can be manufactured from HYTREL that is at least partially impregnated into a High Elongation Carded polypropylene nonwoven manufactured by BBA Nonwovens Inc. of South Carolina, having a basis weight of about 22 grams/meter$^2$. The resulting composite material can provide breathability, Moisture Vapor Transmission Rate (MVTR), from about 2,000 grams per meter$^2$ per 24 hours to about 10,000 grams per meter$^2$ per 24 hours. The thickness of the thermoplastic member 26 can vary from about 10 microns to about 35 microns for a 71% thickness variation, wherein higher degree of breathability can be provided in areas of lower thickness. For example, in the waist area of diaper 10 where greater breathability is desired, the thickness of the thermoplastic member 26 can be less than in other areas of the outer cover 24. From the preceding embodiment one skilled in the art can see a wide range of MVTR variation is possible with this invention and all intermediate values within the full range of about 2,000 grams per meter$^2$ per 24 hours to about 10,000 grams per meter$^2$ per 24 hours are also contemplated.

As disclosed above, the new composite materials can provide desired elastic properties. For example, the waist elastic 14 of the diaper 10 shown in FIG. 1 includes a thermoplastic member 28 to provide desired elasticity of the waist 14, providing desired comfort, gasketing, and sustained fit. The elastic property of the waist elastic 14 can be provided by a variety of thermoplastic elastomeric resins providing elastic properties across the thermoplastic member 28. In one embodiment of the present invention the thermoplastic member 28 can be manufactured from KRATON, styrenic block copolymer, available from Shell Corporation, that is at least partially impregnated into a High Elongation Carded polypropylene nonwoven manufactured by BBA Nonwovens Inc. of South Carolina having a basis weight of about 22 grams/meter$^2$. The resulting composite material can provide elastic force at 200% elongation from about 400 grams/25.4 mm width to about 1000 grams/25.4 mm width. The width 46 of the thermoplastic member 28, generally perpendicular to the direction of stretch forces, can vary from about 2 mm to about 200 mm and the thickness of the thermoplastic member 28 can vary from about 30 microns to about 150 microns for an 80% thickness variation, wherein a greater degree of elastic force can be provided in areas of greater thickness and/or area. For example, in the back waist area 40 of the diaper 10 where a greater elastic force can be desired, the thickness and/or width of the thermoplastic member 28 can be greater than in other areas of the waist 14.

In another example of utilizing elastic properties, the elastic leg cuff 12 of the diaper 10 shown in FIG. 1, includes a thermoplastic member 42 to provide desired elasticity of the elastic leg cuff 12 providing desired comfort and gasketing. The elastic property of the elastic leg cuff 12 can be provided by a variety of thermoplastic elastomeric resins providing elastic properties across the thermoplastic member. In one embodiment of the present invention, the thermoplastic member 42 can be manufactured from KRATON styrenic block copolymer available from Shell Corporation, that is at least partially impregnated into a High Elongation Carded polypropylene nonwoven manufactured by BBA Nonowovens Inc. of South Carolina, having a basis weight of about 22 grams/meter$^2$. The resulting composite material can provide elastic force at 200% elongation from about 50 grams/25.4 mm width to about 100 grams/25.4 mm width. The width of the thermoplastic member 42, perpendicular to the direction of stretch forces, can vary from about 2 mm to about 20 mm and the thickness of the thermoplastic member 42 can vary from about 30 microns to about 150 microns for an 80% thickness variation, wherein a greater degree of elastic force can be provided in areas of greater width and/or thickness. For example, in the back leg area 44 of the diaper 10 where a greater elastic force can be desired, the thickness and/or width of the thermoplastic member 42 can be greater than in other areas of the elastic leg cuff 12.

In yet another example of utilizing elastic properties, the elastic side panel 16 of the diaper 10 shown in FIG. 1 includes thermoplastic member 48 to provide desired elasticity of the elastic side panel 16, providing desired comfort and sustained fit. The elastic property of the elastic side panel 16 can be provided by a variety of thermoplastic elastomeric resins providing elastic properties across the thermoplastic member. In one embodiment of the present invention the thermoplastic member 48 can be manufactured from KRATON styrenic block copolymer available from Shell Corporation, that is at least partially impregnated into a High Elongation Carded polypropylene nonwoven manufactured by BBA Nonwovens Inc. of South Carolina, having a basis weight of about 22 grams/meter$^2$. The resulting composite material can provide elastic force at 200% elongation from about 100 grams/25.4 mm width to about 500 grams/25.4 mm width. The width of the thermoplastic member 48, perpendicular to the direction of stretch forces, can vary from about 2 mm to about 200 mm, and the thickness of the thermoplastic member 48 can vary from about 30 microns to about 150 microns for an 80% thickness variation, wherein a greater degree of elastic force can be provided in areas of greater width and/or thickness.

Figures 5, 6:
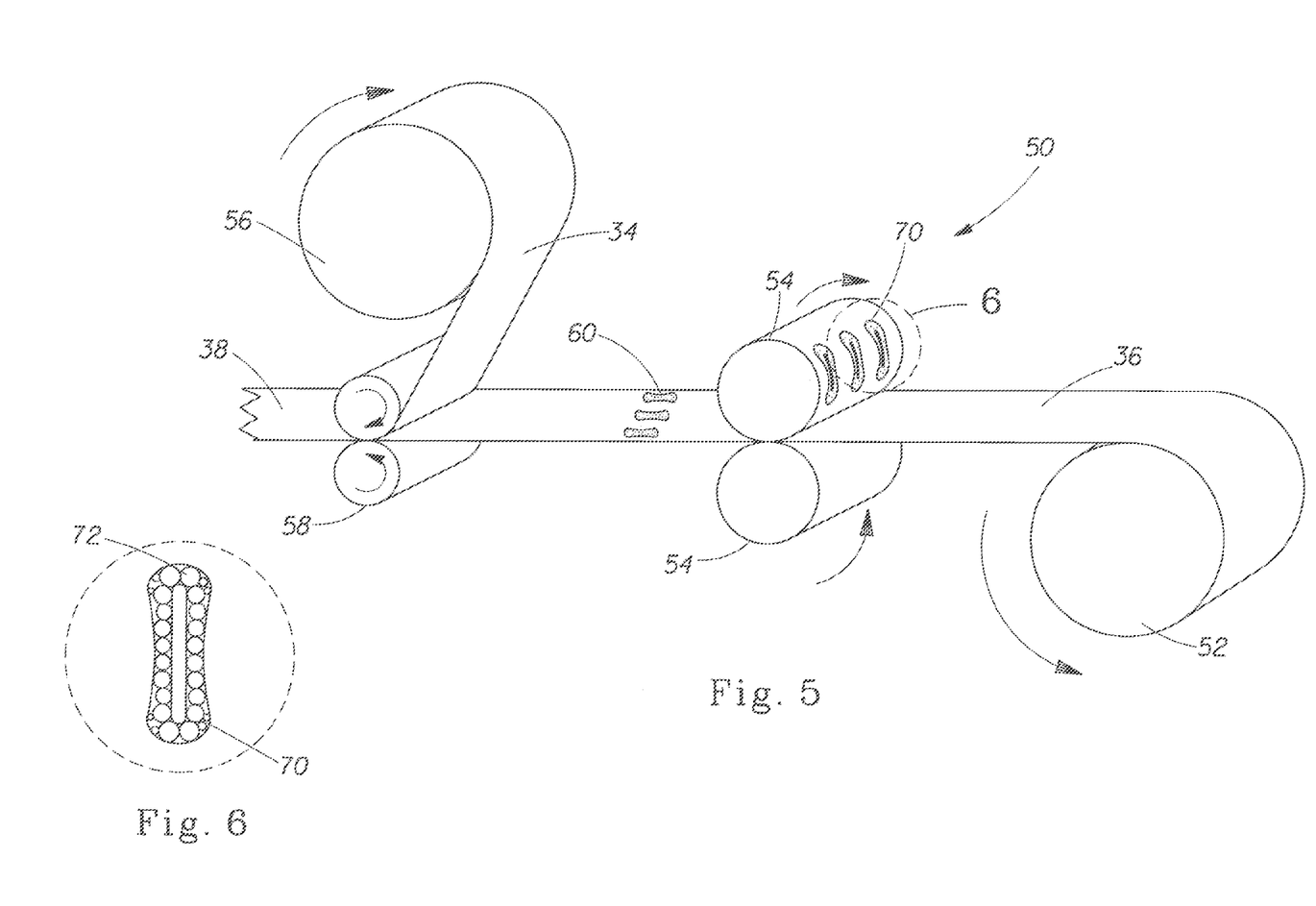
FIG. 5 is a simplified illustration of one embodiment of a process of the present invention for fabrication of a composite material of the present invention.
FIG. 6 is a magnified view of a printing cylinder pattern of the process shown in FIG. 5.

The above composite materials can be manufactured by a process 50 of the present invention, one embodiment of which is illustrated schematically in FIG. 5. The process 50 is capable of at least partially impregnating thermoplastic members into one or more fibrous substrates. The thermoplastic members can be impregnated into the fibrous substrate through a variety of means suitable for supplying and depositing molten thermoplastic resins. The means can include ink jet, spraying, coating, screen-printing, intaglio printing, flexographic printing, and the like. In the preferred embodiment of the present invention, the means of supplying and depositing molten thermoplastic resins can be provided by a rotogravure printing process because it provides flexibility in desired x-y-z dimensions of the thermoplastic member and desired quantity of deposition of the molten thermoplastic resin.

FIG. 5 shows a fibrous substrate 36, which can be provided by a supply roll 52, moving through a rotogravure printing device 54 that deposits molten thermoplastic members 60 onto the fibrous substrate 36 to at least partially impregnate the fibrous substrate 36. Then, if desired, a fibrous substrate 34, which can be provided by a supply roll 56, can be combined with the substrate 36 to cover the molten thermoplastic member 60 and allow the molten member 60 to at least partially impregnate into the substrate 34 to form a composite material 38.

The degree of impregnation of both substrates 34 and 36 by the molten thermoplastic member 60 can be controlled by applying a desired pressure onto the composite material 38 to effect the impregnation. As described above, the substrates 34 and 36 can be any suitable fibrous substrate in any suitable combination. (Alternatively, composite materials of the present invention can include materials, wherein at least one substrate is fibrous. Nonfibrous substrates can include films, foils, foams, and the like.) The source of the pressure can be any suitable means, including contacting or noncontacting means. FIG. 5 shows an example of a contacting means provided by a nip roll pair 58 which can be heated or chilled. Further, the degree of impregnation can be effected by the viscosity of the molten thermoplastic member 60, the porosity of the fibrous substrates 34 and 36, and the surface tension of both the molten thermoplastic member 60 and the fibrous substrates 34 and 36. The rotogravure-printing device 54 can be any suitable conventional thermal rotogravure device. One suitable rotogravure-printing device can be obtained from Roto-Therm Inc. of California.

FIG. 6 illustrates a magnified view of a rotogravure pattern 70 for depositing the molten thermoplastic member 60. As shown, the cells 72 are preferably intersecting with each other to provide a contiguous distribution of the molten thermoplastic member 60 along the rotogravure pattern 70, which result in a contiguous distribution of the molten thermoplastic resin in the thermoplastic member 60.

For example, the composite material 38 (FIG. 2-4) of the slot and tab fastening system 18 (FIG. 1) can be manufactured by the above process 50 (FIG. 5) utilizing two substrates 34 and 36, molten thermoplastic member 60, and subsequent compression of the composite material 38. Further, the breathable region 25 (FIG. 1) of the outer cover 24 can be manufactured by the above process utilizing preferably a single fibrous substrate 36 and a rotogravure pattern of the desired shape (in the form of the breathable region 25). Furthermore, the composite material of the elastic waist 14 and the elastic leg cuff 12 can be manufactured by the above process utilizing either one or more fibrous substrates and respective shapes of rotogravure patterns. Similarly, the composite material of the elastic side panel 16 can be manufactured by the above process using one or more fibrous substrates and respective shapes of the rotogravure patterns.

In addition, the elastic properties of the leg elastic 12, the waist elastic 14, and the side panel elastic 16 can be provided by various secondary operations, including incremental stretching of the composite material to permanently elongate the fibrous substrate to enable the thermoplastic member to stretch within the provided elongation of the substrate. Alternatively, prior to depositing the molten thermoplastic member, the fibrous substrates can be strained to consolidate the fibrous substrate in the cross direction, which after deposition of the molten thermoplastic member, can expand under a force in the cross direction to enable the thermoplastic member to stretch within the provided expansion of the substrate.

Figure 7:
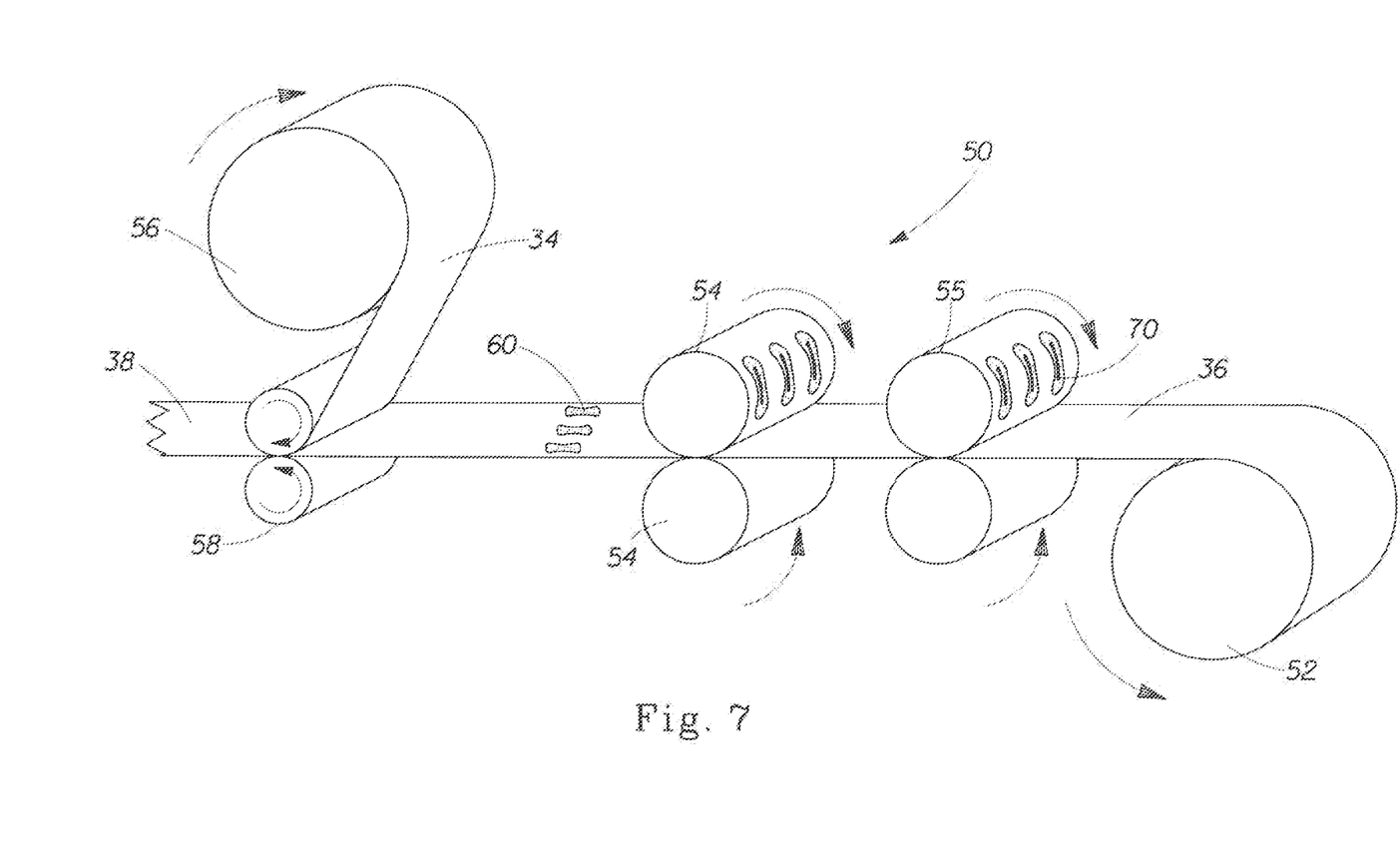
FIG. 7 is a simplified illustration of another embodiment of a process of the present invention for fabrication of a composite material of the present invention.

FIG. 7 illustrates another process embodiment of the present invention showing the use of multiple deposition devices 54 and 55, to provide multiple depositions of one or more thermoplastic materials onto a substrate 36, and then combining with a substrate 34, and/or making several subsequent depositions onto the same substrate.

Figure 8:
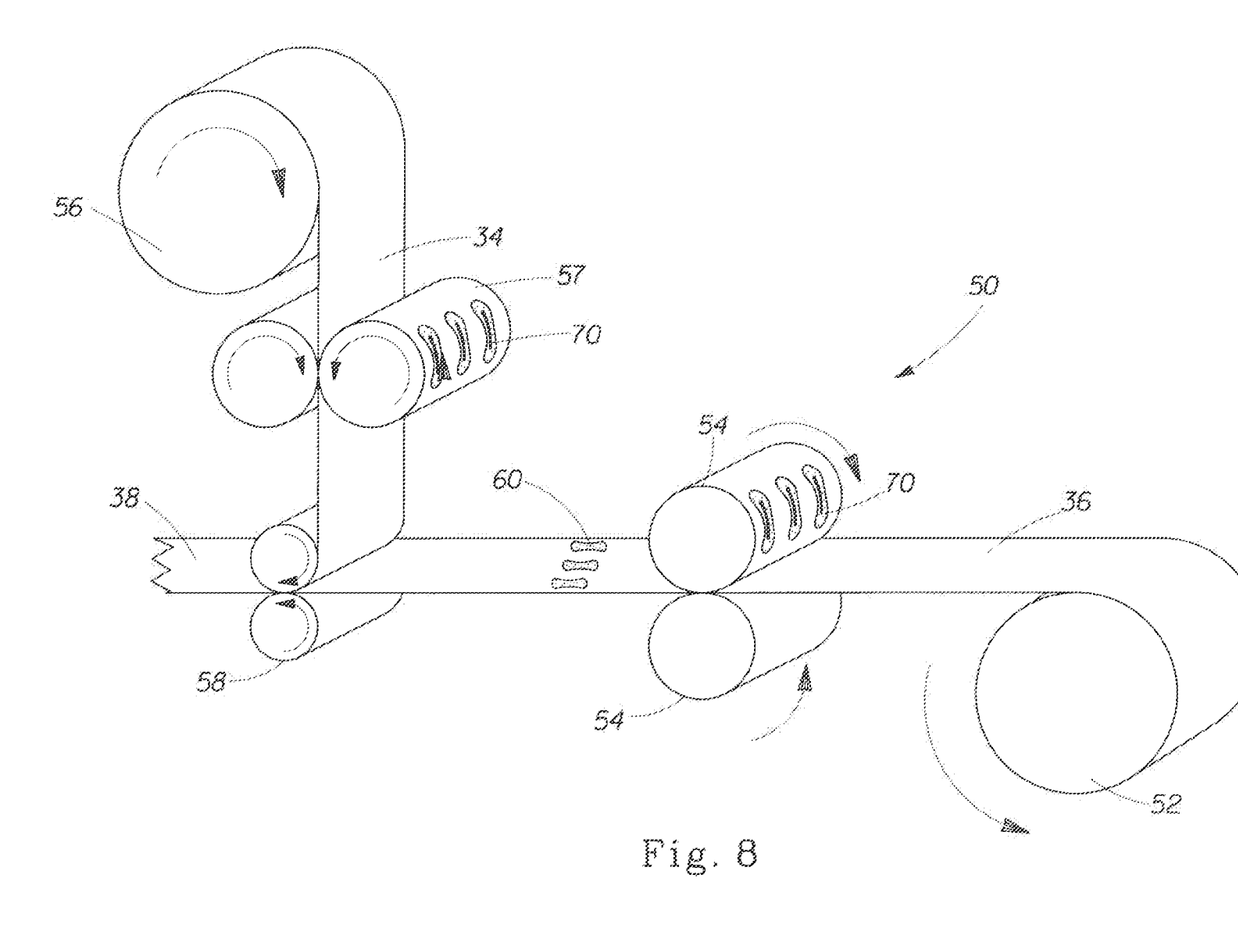
FIG. 8 is a simplified illustration of yet another embodiment of a process of the present invention for fabrication of a composite material of the present invention.

FIG. 8 illustrates yet another process embodiment of the present invention showing the use of multiple deposition devices 54 and 57, to provide multiple depositions of one or more thermoplastic materials onto one or more substrates 36 and 34, including deposition onto two or more substrates separately and then combining them. Further, the use of multiple deposition devices can provide a greater deposition weight of the molten thermoplastic material, a greater z dimension profile variation, capability to deposit different thermoplastic materials, and capability to deposit thermoplastic materials of different colors, and any combinations thereof.

Test Procedures

Liquid Impermeability (Hydro-Head Test)

The test method used by the inventors is the following method derived from ASTM D751 titled Standard Test Method for Coated Fabrics, section titled Pressure Application by a Rising Column of Water, procedure B1.

The test principle is to increase an adjustable water head of distilled water on the top side of a test specimen of about 64 $cm^2$, such as a film or an other porous material.

A test specimen is cut to about 10 cm by 10 cm with a centered O-ring seal of about 8 cm diameter. The sample plate has a centered opening of about 7.6 cm diameter to allow observation of the bottom side of the test specimen during the test. The sample plate is carefully positioned under a 7.6 cm inner diameter Perspex column of about 1 m height, with a mounting flange so as to conveniently allow tightening of the sample plate carrying the sample underneath by means of screws. Optionally, a mirror can be positioned under the opening in the sample plate to ease the observation.

The Perspex column has a sideways-oriented opening of about 1 cm diameter to allow connection to a pump, about 1 cm above the sample when mounted. Optionally, a three-way-valve can be mounted in this connection to allow easier emptying of the column after the test.

The pump is set to raise the liquid head in the Perspex column to 25.4 cm within 60+/−2 seconds. Upon starting of the pump the bottom surface of the test specimen is watched. Upon the first drop of water falling off of the test specimen, the pump is immediately stopped and the height in the Perspex column is recorded in units of mm.

For each material, the test should be repeated for five samples and the results should be averaged.

Tensile Properties

Depending on the thickness and choice of polymeric materials, suitable test methods can include the following methods: ASTM D882 titled Standard Test Method for Tensile Properties of Thin Plastic Sheeting; ASTM D638 titled Standard Test Method for Tensile Properties of Plastics; ASTM D3039/D3039M titled Standard test Method for Tensile Properties of Polymer Matrix composite Materials; and ASTM D76 titled Standard Specification for Tensile Testing Machines for Textiles. Tensile at break data is reported in force per cross sectional area, MPa (Pascal×$10^6$). The cross sectional area is perpendicular to the direction of force.

For each material, the test should be repeated for five samples and the results should be averaged.

Flexural Modulus

The test method used by the inventors is the following method derived from ASTM D790 titled Standard Test Method for Flexural Properties of Unreinforced and Reinforced Plastics and Electrical Insulating Materials. This test method utilizes a three-point loading system applied to a simply supported beam. One suitable test machine, available from Rheometric Scientific Inc. of New Jersey, is the DMTA MkIV. The sample preparation, formulas, and operating range can be found in the DMTA hardware manual 902-50001 Rev A.1 dated January 1997. Flexural modulus data is reported in units of (MPa). The cross sectional area is perpendicular to the bending plane For each material, the test should be repeated for 5 samples and the results should be averaged.

Moisture Vapor Transmission Rate (MVTR)

The test method used by the inventors is the following method derived from ASTM E90 titled Standard Test Methods for Water Vapor Transmission of Materials, section titled Standard Desiccant test method.

A known amount of $CaCl_2$ is put into a flanged cup. A sample material is placed on top of the cup and held securely by a retaining ring and gasket. The assembly is then weighed and recorded as the initial weight. The assembly is placed in a constant temperature (40 deg C.) and humidity (75% RH) for five (5) hours. The assembly is then removed from the chamber and allowed to equilibrate for at least 30 minutes at the temperature of the room where the balance is located. The assembly is then weighed and recorded as the final weight. The moisture vapor transmission rate is calculated and expressed in $g/m^2/24$ hours MVTR=(final weight−initial weight)×24.0)/area of sample in meters^2×5.0 (time in chamber).

For each material, the test should be repeated for 5 samples and the results should be averaged.

Elastic Properties

The test method used by the inventors is the following method derived from ASTM D412-98a titled Standard Test Method for Vulcanized Rubber and Thermoplastic Rubbers and Thermoplastic Elastomers-Tension; ASTM D1566 titled Standard Terminology Relating to Rubber; and ASTM D76 titled Standard Specification for Tensile Testing Machines for Textiles.

Samples of 1" by 3" (25.4 mm by 76.2 mm) size are obtained from the elastic region of the composite. Because the elastic composite has directional properties, which are dependent on the orientation of the sample with respect to the orientation of the elastic members within the sample, samples are prepared with four different orientations. Namely, samples are obtained from the elasticized region with its longitudinal axis aligned in the machine direction (MD), the cross-machine direction (CD), and +/−45 degrees with respect to the machine direction, wherein the machine direction is the substrate movement direction during the process of applying the elastic members to the substrate. At least three samples along each orientation are prepared. If a 1" by 3" elasticized area is not available, the largest possible sample size is used for testing, and the test method is adjusted accordingly. All surfaces of the sample should be free of visible flaws, scratches or imperfections.

A commercial tensile tester from Instron Engineering Corp., Canton, Mass. or SINTECH-MTS Systems Corporation, Eden Prairie, Minn. may be used for this test. The instrument is interfaced with a computer for controlling the test speed and other test parameters, and for collecting, calculating and reporting the data. The tensile properties are measured under typical laboratory conditions (i.e., about 20 degrees C. and about 50% relative humidity). The procedure is as follows:

(1) choose appropriate jaws and load cell for the test; the jaws should be wide enough to fit the sample, typically 1" wide jaws are used; the load cell is chosen so that the tensile response from the sample tested will be between 25% and 75% of the capacity of the load cells or the load range used, typically a 50 lb load cell is used;

(2) calibrate the instrument according to the manufacturer's instructions;
(3) set the gauge length at 1" (25.4 mm);
(4) place the sample in the flat surface of the jaws such that the longitudinal axis of the sample is substantially parallel to the gauge length direction;
(5) set the cross head speed at a constant speed of 10"/min (0.254 m/min) until it reaches 112% strain; then return to the original gauge length at 10"/min (0.254 m/min); and at the end of this pre-straining cycle, start timing the experiment using a stop watch;
(6) reclamp the pre-strained sample to remove any slack and still maintain a 1" (25.4 mm) gauge length;
(7) at the three minute mark on the stop watch, start stretching the sample at a constant speed of 10"/min (0.254 m/min); the instrument records the load versus strain during this cycle; and
(8) calculate and report the load at 200% strain in grams/25.4 mm width.

For the elastic members, the average result of three samples is reported. For the elastic composite, the results from three samples having a given orientation are averaged; the maximum value among those averages is reported as the directional load at 200% strain.

Impregnated Member Thickness

Magnification Method

The test method used by the inventors is the following method derived from ASTM B748 Standard Test Method for Measurement of Thickness of Metallic Coatings by Measurement of Cross Section with a Scanning Electron Microscope and ASTM E766, titled Practice for Calibrating the Magnification of a Scanning Electron Microscope. The test principle is to examine sample cross sections under magnification to determine dimensions such as, thickness, width, or cross sectional area of impregnated polymeric members (excluding non-impregnated portions of a substrate).

A sample containing the impregnated member can be immersed in liquid nitrogen for 30 seconds, and then a cross section, in the plane of the desired dimension, can be cut with a sharp razor from the desired location on the impregnated member. The cross section sample can be mounted onto a conductive tape such as #16084-2 from Ted Pella Inc. of California, and then placed onto a Scanning Electron Microscope (SEM) mount stage. The cross section sample can then be gold plated by using a vacuum plasma-coating unit such as Denton Vacuum DESK II from Denton Inc. of New Jersey using instructions provided by the manufacturer.

The sample can be observed and recorded using the instructions of the manufacturer of the SEM. A suitable SEM test apparatus S-3500N can be available from HITACHI of Japan. The sample can be analyzed and recorded at a magnification from about 50× to about 300×. Magnification is adjusted such that the full length of the dimension of interest is in the field of view. The photomicrograph recorded for each sample can be stored as an electronic file at a resolution recommended by the manufacturer of the SEM.

The photomicrograph electronic file for each sample can be imported into a software application for measuring dimensions, such as Quartz PCI version 4.20 from Quartz Imaging Corporation of Vancouver British Columbia. Because of the roughness of the interface between the impregnated member and the fibrous substrate, multiple measurements in the location of interest are taken and then averaged to determine the dimension. Dimensions can be recorded to the nearest 10 microns.

For each cross sectional sample, five typical locations for the dimensions of interest should be measured and the results should be averaged.

Basis Weight

The test method used by the inventors is the following derived from ASTM D646, titled Standard Test Method for Grammage of Paper and Paperboard (Mass Per Unit Area).

Ten samples of the test material are cut to the desired dimensions (10 cm×10 cm) with a precision (+/−0.1 mm) die rule press. The samples are laid onto a calibrated gravimetric scale that reads to the nearest 0.001 grams. The weight of the 10 samples can be multiplied by 10 and recorded as basis weight in grams/meter$^2$.

Dynamic Fluid Impact Test

The dynamic fluid impact test method set forth below is designed to mimic the energy per area that an infant imparts to a diaper backsheet when abruptly going from a standing to a sitting position.

Figure 9:
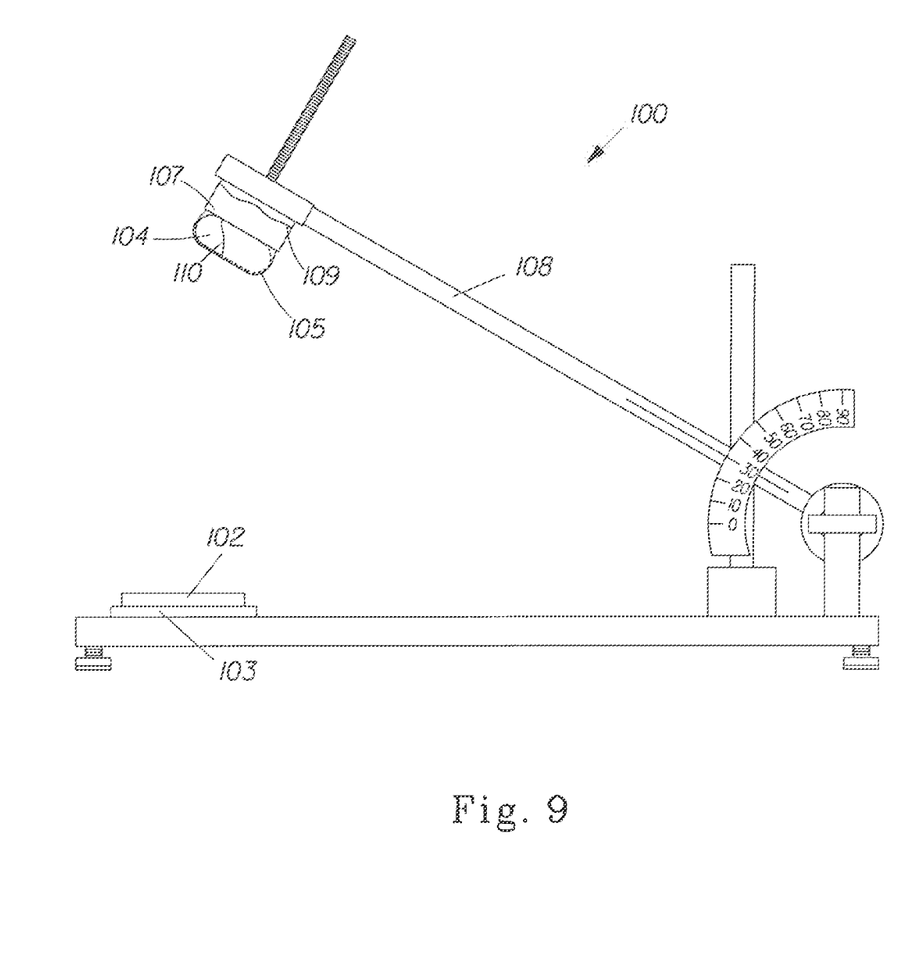
FIG. 9 is a simplified illustration of an apparatus used for determining the dynamic fluid transmission value.

The dynamic fluid impact test method utilizes the apparatus 100 shown in FIG. 9. An absorption material 102 weighed to the nearest 0.0001 gram is placed directly on top of the energy absorbing impact pad 103. To this purpose, the absorption material 102 can comprise a No. 2 filter paper available from Whatman Laboratory Division, Distributed by VWR Scientific of Ohio. The absorption material should be able to absorb and retain the simulated urine, which passes through the backsheet material being tested. The energy absorbing impact pad 103 is a carbon black filled cross linked rubber foam. The about 5 inch by about 5 inch (125 mm by 125 mm) square impact pad has a density of about 0.1132 grams/cm$^3$ and a thickness of about 0.3125 inches (7.9375 mm). The impact pad 103 has a Durometer Value of A/30/15 according to ASTM 2240-91.

A circular absorbent core material 104 measuring about 2.5 inches (63.5 mm) in diameter is weighed. To this purpose, the absorbent core material can comprise individualized, crosslinked wood pulp cellulosic fibers as described in U.S. Pat. No. 5,137,537 issued to Herron et al. on Aug. 11, 1992. The absorbent core has a basis weight of about 228 grams/m$^2$. The absorbent core material is then loaded with simulated urine to about (10) times its dry weight. This represents an absorbent core sufficiently loaded with urine. The absorbent core material should be able to hold a sufficient amount of simulated urine, e.g., at least about ten times its dry weight. Accordingly, other absorbent core materials currently used in commercial diapers may also be used as the absorbent core material. The simulated urine can comprise distilled water.

A section of the backsheet material 105 to be tested is placed face down with the outside surface on a clean and dry tabletop. The loaded core material 104 is placed directly in the center of the backsheet material 105. The backsheet/core arrangement is then secured to the impact portion 107 of the impact arm 108 with a rubber band 109. The backsheet/core arrangement is positioned such that the core 104 is adjacent to the bottom surface 110 of the impact portion 107. The impact arm 108 is raised to a desired impact angle to provide the desired impact energy. The impact arm 108 is then dropped and a stopwatch is activated on impact. The arm then rests on the filter paper 102 for ten seconds. The impact arm 108 is then raised and the filter paper 102 is removed and placed on a digital scale. The mass of the wet filter paper is recorded at the three minute mark. The dynamic fluid transmission value (DFTV) is calculated and expressed in grams/m² at a specific impact energy expressed in Joules/m² using the following formula:

DFTV=(mass of wet filter paper−mass of dry filter paper)/impact area

The impact area, expressed in m², is the area of the bottom surface 110 of the impact portion 107. The impact area is 0.00317 m². The absorbent core material 104 should have an area slightly larger than that of the impact area of the surface 110.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A method of making a composite material comprising at least one shaped thermoplastic member impregnated into at least one fibrous substrate, the method comprising the steps of:
    providing a first fibrous substrate;
    depositing a first thermoplastic material on the first fibrous substrate using a rotogravure printing device to form a first shaped thermoplastic member having a profiled thickness providing variation in material properties, wherein a percent variation of the profiled thickness of the thermoplastic member can vary from about 5% to about 95%;
    providing a second substrate;
    depositing a second thermoplastic material on the second fibrous substrate to form a second shaped thermoplastic member;
    combining the first substrate and the second substrate to form the composite material, wherein the first thermoplastic member is at least partially impregnated into the first substrate; and
    impregnating the first and second shaped thermoplastic member into the first and second substrates by advancing the composite material through a pair of nip rolls.

2. The method of claim 1, wherein the thermoplastic material is at least partially impregnated into the second substrate.

3. The method of claim 1, wherein the percent variation varies from 20% to 80%.

4. The method of claim 1, wherein the second substrate is not fibrous.

5. The method of claim 1, wherein the second substrate is fibrous.

6. The method of claim 1 wherein the step of depositing is selected from a group consisting of intaglio printing, gravure printing, screen-printing, ink jet printing, and flexographic printing.

7. The method of claim 6, wherein the first thermoplastic member and the second thermoplastic member are different materials.

8. A method of making a composite material comprising at least one shaped thermoplastic member impregnated into at least one fibrous substrate, the method comprising the steps of:
    providing a first fibrous substrate;
    depositing a first thermoplastic material on the first fibrous substrate using a to form a first shaped thermoplastic member having a profiled thickness providing variation in material properties, wherein a percent variation of the profiled thickness of the thermoplastic member can vary from about 5% to about 95%;
    providing a second substrate;
    depositing a second shaped thermoplastic member on the first fibrous substrate on top of the first shaped thermoplastic member;
    combining the first substrate and the second substrate to form the composite material, wherein the first thermoplastic member is at least partially impregnated into the first substrate; and
    impregnating the first and second shaped thermoplastic member into the first and second substrates by advancing the composite material through a pair of nip rolls.

9. The method of claim 8 wherein the step of depositing the second shaped thermoplastic member is selected from a group consisting of gravure printing, screen-printing, ink jet printing, and flexographic printing.

10. The method of claim 8, wherein the first shaped thermoplastic member and the second shaped thermoplastic member are different materials.

11. The method of claim 8, wherein the first shaped thermoplastic member and the second shaped thermoplastic member are same materials.

* * * * *